United States Patent [19]

Moore

[11] Patent Number: Plant 6,618

[45] Date of Patent: Feb. 21, 1989

[54] ROSE PLANT / VAR.: MORFIRE

[75] Inventor: Ralph S. Moore, Visalia, Calif.

[73] Assignee: Sequdia Nursery, Visalia, Calif.

[21] Appl. No.: 91,736

[22] Filed: Aug. 31, 1987

[51] Int. Cl.[4] ..... A01H 5/00

[52] U.S. Cl. ..... Plt./7

[58] Field of Search ..... Plt./7

*Primary Examiner*—Robert E. Bagwill

[57] ABSTRACT

This invention relates to a new and distinct variety of miniature rose plant primarily identified by its very double flowers with the petals being yellow tipped red.

1 Drawing Sheet

1

The present invention relates to a new and distinct variety of hardy, dwarf, bush type rose plant of the miniature class; the variety being primarily characterized — as to novelty — by the very double flowers, the petals being generally deep yellow tipped with red.

The variety is further characterized by:

An abundance of bloom, with flowers usually borne singly, but also several to the stem in loose cluster or spray.

Little or no fragrance.

A plant which is vigorous, of rounded to upright shape with small semi-glossy foliage with pointed leaflets; the buds and flowers being similar in form to Pink Petticoat (miniature — U.S. Plant Pat. No. 4,636).

The plant, which has a normal height of 14–16 inches, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at Sequoia Nursery, located at Visalia, Calif., under conditions of careful control and observation, as a cross between Pink Petticoat (U.S. Plant Pat. No. 4,636 — miniature) as the seed parent and Gold Badge (Meigronuri — Floribunda — U.S. Plant Pat. No. 4,625) as the pollen parent.

Subsequent to origination of the variety I successfully asexually reproduced it at Sequoia Nursery, located as aforesaid, by budding as well as by cuttings; the reproductions having run true in all respects.

The color photograph illustrates the variety including the foliage, buds and flowers.

Referring now specifically to the new and distinct variety of miniature rose plant, the following is a detailed description thereof in outline; all major color plate identifications being by reference to The British Colour Council Horticultural Colour Chart, except where common terms of color definition are employed.

Type: Hardy; dwarf; bushy; upright; seedling; greenhouse; outdoors; cut flowers; garden decoration; potted plant.

Class: Miniature. Variety identification: Morfire (Commercial synonym: Ring Of Fire).

Flowers borne: Singly and several together in loose clusters or spray on sturdy, wirey stems.

Quantity of bloom: Abundant both outside and in greenhouse.

Bud:

2

*Peduncle.*—Medium length; slender but sturdy; erect; medium green, sometimes tinted bronze (outdoors); nearly smooth or with some small hair-like apendages. Before calyx breaks; size — small.

*Form.*—Ovoid to pointed, with several small foliaceous apendages on surface of bud; with foliaceous parts extending beyond the tip of the bud equal to more than one-half of its length.

*Color.*—Medium green, occasionally tinted with bronze (outdoors). As calyx breaks, color — yellow with red on petal tip.

*Opening.*—Opens well in all weather.

Bloom:

*Size when fully open.*—Small, averaging about 35 mm (1½").

*Petalage.*—Very double — averaging about 65 (or more) petals, arranged regularly plus several small petaloids.

*Form.*—Full, high centered — first becoming rounded with petals rolled loosly outward and downward. Open flowers usually have no stamens.

Petals: Fairly thick; satiny on inside and on outside surface.

*Shape.*—Outside petals, broad lanceolate (wedge shaped) with rounded tip; intermediate — broad lanceolate with nearly round or short acute tip; inside — lanceolate with acute tip.

Color: Newly opened flower from a plant grown outdoors (August 1987), Visalia, Calif.

*Outside petal.*—Outside surface — yellow (near Saffron Yellow 7/2) edged or tipped with red. Inside surface — near Indian Yellow 6/1 or Saffron Yellow 7/2 with petal edged or tipped with red (wider than on reverse with the red banding sometimes blending or bleeding into the yellow color.

*Intermediate petal.*—Outside surface similar to outside petal. Inside surface similar to outside petal.

*Inner petal.*—Outside surface similar to intermediate petal; inside surface — similar to intermediate petal. General color effect; newly opened flowers — orange (a red on yellow effect). Three days open — color — similar to fresh open flower, but less bright. Behavior — opens well in all weather. Spent petals or flowers drop off. Flower longevity (July–August 1987) — plant in pot 8–10 days or longer. Cut flowers at living room temperature 5–7 days or longer.

Reproductive organs:

*Stamens.*—Usually none.
*Filaments.*—Usually none.
*Anthers.*—Usually none.
*Pollen.*—None.
*Pistils.*—Small number.
*Styles.*—Short length; reddish; bunched.
*Ovaries.*—All enclosed in calyx.
*Hips.*—None.
*Sepals.*—Permanent; spear shaped; recurved.
*Seed.*—None.

Foliage:

*Leaves.*—Compound of five (sometimes three or seven) leaflets; medium small; leathery; semi-glossy.

*Leaflets.*—Shape: broad lanceolate; apex acute; base — acute — sometimes rounded. Color: medium green; new growth — normal (medium) green (sometimes tinted reddish). Rachis: medium strength; upperside may have a few short hairs; grooved; underside may have several small thorns (or claws) and few to several tiny short prickles. Stipules: medium to short length; medium width; medium to short length narrow points which turn out usually at about 45 degrees or more.

Growth:

*Habit.*—Dwarf; bushy; upright; much branched.
*Growth.*—Vigorous; internodes short.

*Canes.*—Medium; slender; sturdy.
*Main stems.*—Color: medium green.
*Thorns.*—Average, of varying size and length — slightly hooked or inclined downward. Hairs — few or none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, bushy, upright, much branched habit, substantially as illustrated and described, characterized by buds and flowers, basically yellow and edged with red, the bud being pointed in the early opening stage, resembling in form Pink Petticoat (Miniature — U.S. Plant Pat. No. 4,636) with the open flower being very full (double) and rounded with many (65 or more) petals; and further characterized by a plant of compact, vigorous, upright shape, with main stems and shoots of average thorniness, the said plant being easy to propagate from soft wood cuttings with an abundance of small semi-glossy foliage, the flowers being borne singly or several together in loose clusters or spray on medium length stems.

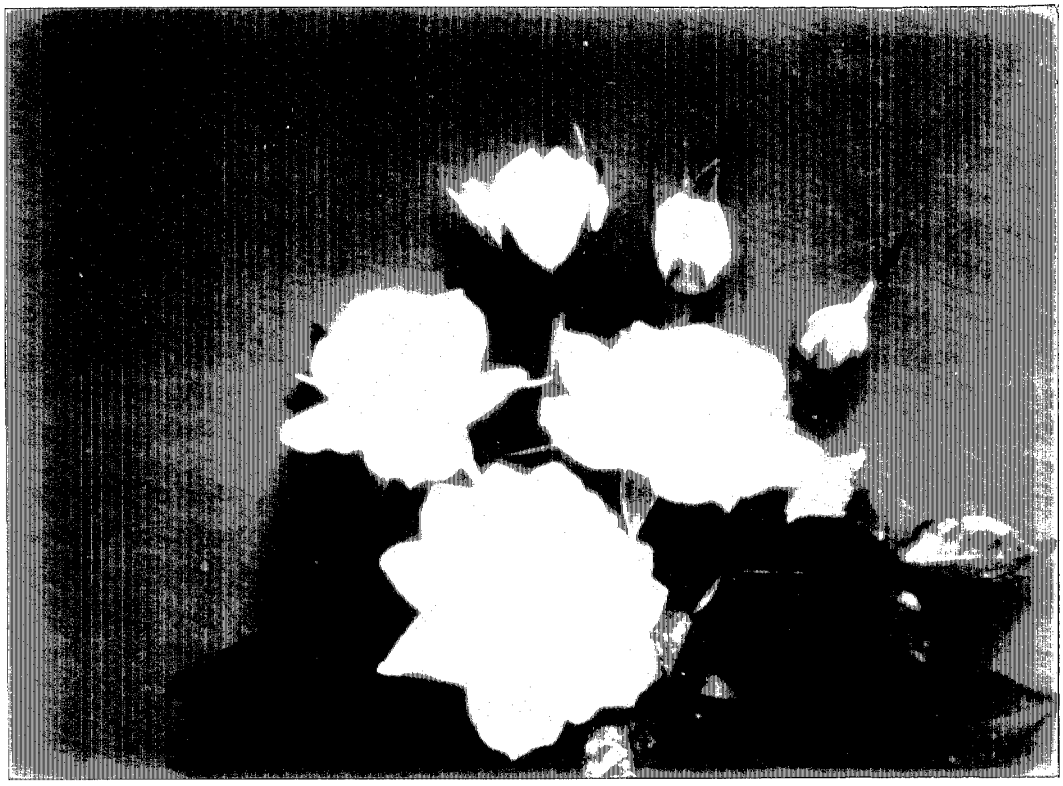

* * * * *